United States Patent [19]

Brown et al.

[11] Patent Number: 4,952,406

[45] Date of Patent: Aug. 28, 1990

[54] FEEDBACK CONTROLLED RELEASE

[75] Inventors: Larry Brown, Brookline; Fariba Fischel-Ghodsian, Boston; Robert S. Langer, Somerville, all of Mass.

[73] Assignee: The Children's Medical Center Corporation, Boston, Mass.

[21] Appl. No.: 36,158

[22] Filed: Apr. 3, 1987

Related U.S. Application Data

[63] Continuation of Ser. No. 749,946, Jun. 27, 1985, abandoned.

[51] Int. Cl.$^5$ .................... A61K 37/26; A61F 2/00
[52] U.S. Cl. ........................ 424/425; 514/3; 514/2
[58] Field of Search ............ 514/3; 424/425, 2

[56] References Cited

U.S. PATENT DOCUMENTS 4,164,560 8/1979 Folkman et al. .................. 424/22
4,357,312 11/1982 Hsieh et al. ....................... 424/15
4,364,385 12/1982 Lossef ............................... 424/19

OTHER PUBLICATIONS

Lym, Science (1980) 210:908.
Levy and Carpenter, *Biochemisty*, vol. 6, No. 11, Nov. 1967.

*Primary Examiner*—Frederick E. Waddell

[57] ABSTRACT

A controlled release system using a feedback-responsive controller reversibly changes the pH of the aqueous microenvironment of a biologically active compound sequestered in an aqueous-fluid-penetrable, aqueous-insoluble biocompatible material; the pH change is effected in response to a change in the concentration of the target compound in the aqueous medium surrounding the insoluble material; as a result of the pH change, the aqueous solubility and therefore the release rate of the active compound is reversibly changed.

25 Claims, 1 Drawing Sheet

FEEDBACK CONTROLLED RELEASE

This is a continuation of co-pending application Ser. No. 799,946 filed on June 27, 1985, now abandoned.

BACKGROUND OF THE INVENTION

This invention relates to the controlled release of a biologically active compound to an aqueous medium where the active compound participates in altering a target compound—e.g., in vivo release of a hormone to the blood stream of a mammal where it regulates the metabolism of a target metabolite.

Various systems for controlled release of a biologically active compound to an aqueous medium are known. For example, Folkman et al. U.S. Pat. No. 4,164,560, and Hsieh et al. U.S. Pat. No. 4,357,312 describe polymeric bodies that can be implanted, in vivo, to provide controlled sustained release of drugs. Such systems generally provide release at a constant rate over a long period of time.

The amount of a drug such as insulin that is needed may vary widely during the course of the day and, in many controlled release situations, it is desirable to provide higher levels of the active compound when it is specifically needed, and to conserve the active compound at other times. Specifically, insulin is required in relatively large doses immediately after a meal, and it is possible that some of the serious long-term complications that diabetics suffer result from an inability to regulate the amount of insulin being administered, with the result that, for a significant period of each day, the patient experiences either too much insulin or a build-up of metabolites from too little insulin.

Folkman et al. USSN No. 290,729, filed Aug. 6, 1981, discloses one approach to this problem in which magnetically responsive particles are included within the polymer matrix, and a temporary increase in the release of a drug such as insulin is effected by subjecting the polymer matrix to an oscillating magnetic field. Another approach involves the use of pancreatic beta cells encapsulated in a biocompatible membrane and implanted subcutaneously. Lym, Science (1980) 210:908. The normal feedback mechanism of the cells controls the amount of insulin they provide.

Lossef U.S. Pat. No. 4,364,385 discloses release of insulin contained within a semipermeable membrane that includes glucose oxidase and catalase. Glucose levels outside the membrane alter the charge of the membrane via glucose oxidase activity, thus changing the membrane's permeability to insulin.

SUMMARY OF THE INVENTION

The invention features a controlled release system using a feedback-responsive controller that changes the pH of the aqueous microenvironment of a biologically active compound sequestered in an aqueous-fluid-penetrable, aqueous-insoluble biocompatible material; pH change between a first level and a second level is effected in response to a change in the concentration of the target compound in the aqueous medium surrounding the insoluble material; as a result of the pH change, the solubility of the active compound is changed reversibly between a first and second level, and its rate of release to the surrounding aqueous fluid thereby is changed in a reversible way. By "aqueous" we mean to include not only water, but any aqueous biological fluid such as blood or lymph. By "microenvironment", we mean the aqueous fluid sufficiently proximate to the active substance that pH changes therein will be reflected in the properties of the active substance (e.g., for a protein, the net charge changes) and thereby will effect the change in solubility and release rate.

In preferred embodiments, the feedback-responsive controller is made up of: (1) an operator (e.g. an enzyme) sequestered by the insoluble material; and (2) a signal (e.g. a substrate for the enzyme) representative of the target compound concentration in the surrounding aqueous medium. The signal communicates between the medium and the operator, and the operator responds to the signal to change the pH of the microenvironment of the sequestered biologically active compound (e.g. by build-up of the product of the enzymatic reaction). The feedback controller can include a cascade element that responds to a change in pH by effecting a further pH change in the same direction. When the target compound serves as the signal, the pH change effected increases the release rate to respond to an increase in the target compound concentration. The insoluble material may be a semipermeable membrane that allows passage of the dissolved active compound, but not the operator or agglomerated active compound; alternatively and preferably, the insoluble material is a polymer matrix, and the active compound is a drug interspersed in the matrix, such as the drugs disclosed in Folkman et al. U.S. Pat. No. 4,164,560, which is hereby incorporated by reference. The biologically active compound is agglomerated in a form that restricts its ability to pass through the polymer matrix, and the pH change alters its solubility and therefore its ability to pass through the matrix. The system is adapted to be implanted in vivo in a mammal, e.g. to release a hormone to circulating blood, the target compound alteration being an intracellular process regulated by the hormone. Preferred hormones include insulin, glucagon, growth hormone, lutinizing hormone, and releasing hormone. Where the biologically active compound is an insulin, it can be released at a rate governed by the concentration of glucose using an enzyme, such as glucose oxidase, that operates on glucose. By "an insulin", we mean a protein hormone identical to a mammalian insulin or modified therefrom, but retaining at least 10% of the activity of the natural insulin. The insulin preferably is modified if necessary to change its isoelectric point to pH 7.0 or greater, the feedback controller being able to change the pH of the microenvironment from a first range around its isoelectric point (about 7.1 to 7.5) to a second range sufficiently below 7.0 to increase the insulin's solubility over its solubility in the first range.

The system provides feedback control of the release rate of the biologically active compound, so that the compound is available as needed and is conserved when it is not needed, thus prolonging the release period and improving the match between the release rate and the need for the active compound. Such a system approximates natural feedback regulatory controls and can help to reduce the chance of undesirable swings in target compound concentration, e.g. buildup from excessively slow release or depletion from excessively rapid release.

Other features and advantages of the invention will be apparent from the following description of the preferred embodiment and from the claims.

DESCRIPTION OF THE PREFERRED EMBODIMENT

Figure 1:
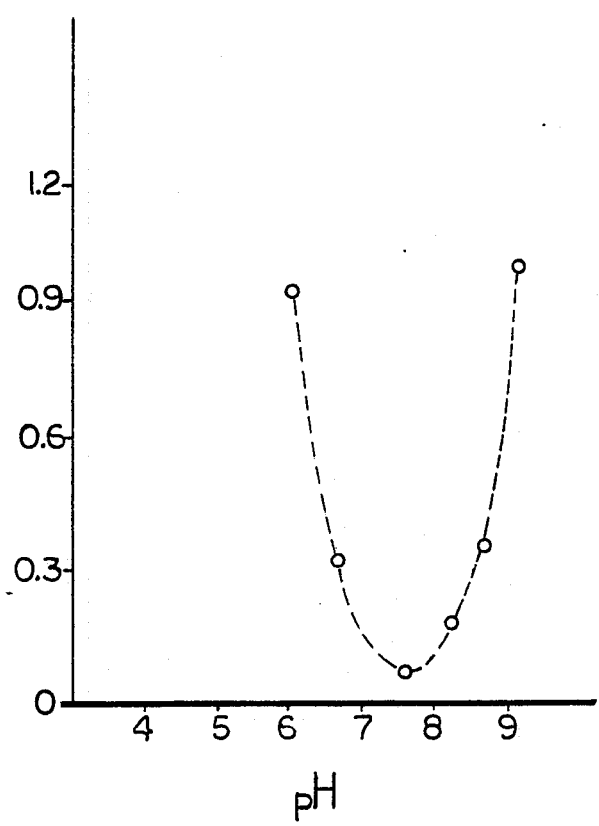

The following description of the structure, manufacture, and use of a feedback-controlled insulin release system to be implanted in vivo is illustrative. We first briefly describe the drawing.

DRAWING

FIG. 1 is a graph of the solubility of trilysine insulin versus pH.

STRUCTURE

The preferred biocompatible, aqueous-insoluble material allows aqueous fluids to penetrate to reach the sequestered active substance. A variety of aqueous-insoluble materials are suitable, and the preferred materials are polymer matricies that have a limited (less than 50% by weight) aqueous fluid sorptivity and that are plastically deformable in response to aqueous sorption by the active compound. Many suitable such polymer matricies are disclosed in the above-referenced Folkman et al. '560 patent. Particularly preferred insoluble materials are olefin vinyl ester copolymers such as ethylene vinyl acetate copolymers.

The preferred feedback controller is an enzyme, sequestered together with the active substance, that operates on a target compound. For an insulin release system, the glucose/glucose oxidase system is preferred, and the glucose oxidase is immobilized on sepharose beads to prevent its release. Bacterial glucose oxidase has a molecular weight of 150,000 to 180,000, and is active through a broad pH range. It is relatively stable and specific for beta-D-glucose yielding glucono lactone and hydrogen peroxide from that substrate. The glucono lactone is then converted to gluconic acid, thus decreasing the pH in the microenvironment of the active substance. A suitable source of glucose oxidase Sigma Chemical Co., St. Louis or isolation from *Aspergillus niger*.

When using the glucose/glucose oxidase system, it is desirable to avoid detrimental effects on system components, or on the tissue surrounding the implant, due to build-up of hydrogen peroxide. One way to do this is to include within the polymer system a second enzyme such as catalase that converts hydrogen peroxide to water and molecular oxygen. The catalase can be obtained from Sigma Chemical Co., and it can be included in the polymer matrix by immobilizing it either to the polymer or to sepharose as described below for catalase.

The biologically active compound may be any of a large number of drugs that respond to pH changes in a surrounding aqueous environment. For example, proteins characteristically are least soluble at their isoelectric point and become more charged and soluble as the pH is changed away from the isoelectric point in either direction. Folkman et al. U.S. Pat. No. 4,164,560 lists a large number of proteins that can be used in a feedback-regulated release system. Protein hormones such as insulins are particularly adapted for controlled release in response to the concentration of a substance whose modification (e.g. metabolism) they regulate.

The following description of selecting the insulin to be used is generally applicable to other active substances to be released. The insulin used is selected to have a solubility that changes significantly at pH levels that can be induced by the feedback controller used. First, the isoelectric point of the insulin is determined (if it is not known) to establish the point of minimum solubility. A suitable method for determining isoelectric points is to use a focusing model FBE-3000 from Pharmacia, Piscataway, N.Y. Then, the effect of pH changes away from the isoelectric point on release rate can be determined by exposing identical polymer release systems to different pH's and assaying for insulin released by radioimmunoassay. The ability of the feedback controller to change the microenvironment pH when the system is embedded in a fluid having a physiological pH can be determined using a microelectrode such as SA-1 pH electrode, with a Merle reference (World Precision Instruments, New Haven, CT). The above determinations then are used to select a suitable insulin whose solubility changes significantly over the ranges made available by the feedback controller.

When using the glucose/glucose oxidase in a system to release an insulin to mammalian blood, lymph or other fluid having a pH near neutrality, the preferable insulins are those with an isoelectric point of above pH 7.0, and most preferably above about 7.3. Suitable modified insulins are trilysine insulin which has an isoelectric point at about pH 7.4, or triglycine insulin, which has an isoelectric point over pH 7.4. The effect of pH on solubility of trilysine insulin is shown in FIG. 1, the vertical axis being solubility in mg/ml. Trilysine insulin may be prepared by the general method of Levy and Carpenter (1967) Biochem. 6:3559–3568. The glucose/glucose oxidase system described above will lower pH from about 7.0 to about 6.0, effecting a significant increase in the release of an insulin having an isoelectric point above 7.0. The release rate differential can be increased further using a cascade element that responds to pH change oppositely to buffering, i.e., by effecting a further pH change in the same direction. Poly lactic acid is such a cascade element.

To insure adequate activity, the insulin selected is measured by any of a variety of techniques such as the radioimmunoassy using a double antibody technique.

Other characteristics of the preferred system can be determined from the following description of how to make and use it.

FABRICATION

Sepharose beads (6% cross-linked from Pharmacia Fine Chemicals) are washed with distilled water and dried. One ml. of 60% acetone is added per gram of beads and the resulting slurry placed at $-12°$ to $-15°$ C. One-quarter ml. of one molar cyanogen bromide (in acetone, acetonitrile or dimethyl formamide) is added per gram of beads while stirring, and a similar volume of TEA buffer (about 0.2 M Tris, EDTA and sodium acetate, pH 8) is slowly added. The resulting beads are poured into 100 ml. of 0.1 N HCl at 0° C. and stored for at least about one hour.

To insure the activity of the beads produced, the presence of cyanide is assayed by the Konig assay. Konig reagent is prepared by adding 750 ml. of dimethyl barbituric acid to 45 mls. of pyridine and made up to 50 mls. with water. Three (3.0) ml of the Konig reagent is added to 100–200 mg of dry beads, followed by heating for 15 minutes at 37° C. with vortexing every 5 minutes. The active beads become dark violet and are transferred to 500 ml. of distilled water and the absorbancy of the resulting solution measured at 588 nm after shaking. Activity is calculated by multiplying the absorbance by 3725 and dividing by the milligrams of beads used in the assay, yielding activity in micromoles of cyanide per gram of beads.

The activated beads are washed in distilled water at 0° C. until the pH is approximately 5.8. One ml. of glucose oxidase solution, at 10 milligrams per ml. in bicarbonate buffer at PH 8, is added per gram of beads and the solution placed shaking at 4° C. overnight. After washing these beads in 0.5 molar NaCl in phosphate buffer [e.g., about 0.5 M] at pH 8, and then in 0.1 molar sodium chloride in phosphate buffer at pH 6.5, they are finally washed with distilled water and lyophilized to give a fine powder.

The amount of bound enzyme is readily determined by the Biorad protein assay. Eight hundred ml. of beads is added to 200 ml. of the Biorad dye, vortexed for 5 minutes and the absorbance at 595 nm measured. Protein concentration is estimated from a standard curve.

Preparation of the polymer matrix is described in Folkman et al. [U.S. Pat. No. 4,164,560] and entails a solvent casting method. Ethylene vinyl acetate [EVA]is washed in alcohol or acetone and then dissolved in methylene chloride [10% weight per volume]. Insulin powder and immobilized glucose oxidase, prepared as above, both with particle sizes smaller than 150 microns, are mixed homogeneously [the ratio of insulin to immobilized enzyme is preferably 3 to 2] and added to the polymer solution, in which they are insoluble. This mixture is vortexed and poured into a mold [4×4×1 cm] which is precooled by placing it on a dry ice slab for 15 minutes. The suspension congeals and is then placed at −20° C. for two days, vacuum dried at room temperature for two days and then matrices are excised from the flat polymer with a cork borer [0.5 cm diameter]. The matrix may also include a pH cascader characterized in that a change in the pH at the cascader in a given direction causes the cascader to effect additional change in pH in the same direction. Polylactic acid is such a pH cascader and may be incorporated in the polymer as a powder together with the insulin.

USE

The system described above can be tested to determine the release of insulin under different conditions. The assays and methods used are well known to those skilled in the art. The presence of insulin was measured either by its UV absorbance, by HPLC, or by the use of radioactively labeled insulin. Release of the active substance from an EVA matrix is linear to the square root of time. Glucose oxidase converts glucose into gluconic acid with a resultant lowering in pH from 7.4 to 6.0 within two hours. The pH slowly increases again when the glucose is removed. Trilysine insulin released from the matrix is increased in the presence of glucose, and an insulin with a higher isoeletric point, e.g. triglycine insulin, will have an even greater increase in release rate over that pH range.

Use of the system is demonstrated in female sprague dawley rats induced to become diabetic by streptozoticin injection at a dosage of 65 mg/kg body weight, according to the method of Jurod et al. (1967) PSEBM 126:201-205. Polymer matrices are sterilized by UV light, washed and inserted between connective tissue layers in the skin of the rats. Blood and urine glucose levels are followed, as is the level of trilysine insulin. When treated with a trilysine insulin/glucose oxidase implant, the release of trilysine insulin to the rats' blood stream will respond in a direct relationship to their blood glucose levels.

The precise level of trilysine or triglycine insulin to be loaded in an implant for a specific patient will depend on the patient's need for, and response to, the insulin. These factors can be determined by first administering the chosen insulin by injection to establish its activity in the subject, and then establishing the release levels to a medium that is characterized by physiological pH and glucose levels. The implant can be made in any accessible tissue.

OTHER EMBODIMENTS

Other embodiments are within the following claims. For example, the sources and types of insulin and glucose oxidase used can be varied as can the polymeric matrix used to enclose them. The location of insertion of the device into a body can be any accessible site. The ratio of insulin to glucose oxidase may be varied according to a diabetic's requirements; increases in glucose oxidase will increase the release rate differential, e.g. for diabetics who require a larger differential. Other protein hormones that operate in mammals by participating in a system for changing a metabolite or producing a metabolite can be used. Other polymer systems or insoluble sequestering elements can be used. For example, a semipermeable membrane that will pass the dissolved active compound and the signal compound, but not the enzyme and the cascading element, will serve to contain undissolved active compound, particulary if it is agglomerated to reduce the surface area available to aqueous fluid. Specific insoluble polymeric sequestering materials include in addition to EVA: nitrocellulose, silicone, hydrogels, poly-2-hydroxy ethyl methylmethacrylate, polyesters, polyurethanes, and other polymers approved for use in humans.

We claim:

1. A system providing feedback-responsive release of a protein to an aqueous biological fluid, wherein said protein participates in changing the concentration of a component of said fluid, said system comprising:

(a) said protein, which is selected to have an aqueous solubility at a first level when the pH of the aqueous microenvironment of said protein is in a first pH range, and an aqueous solubility at a second level higher than the first level when said microenvironment pH is in a second pH range;

(b) an aqueous-insoluble biocompatible material positioned to sequester said protein, said protein and said insoluble material being characterized in that said insoluble material is aqueous-fluid-penetrable, allowing controlled release of said sequestered protein therefrom, and changes in said aqueous solubility from said first to said second level effecting an increase in the rate of release of said sequestered protein from said insoluble biocompatible material; and (c) an enzyme catalyzing a reaction capable of causing the pH of the microenvironment of said sequestered protein to change between said first pH range and said second pH range, responsive to concentration changes of said component in said aqueous biological fluid, said enzyme and said protein being further characterized in that concentrations of said component characteristic of an increased demand for said protein in said biological fluid cause the enzyme to change said microenvironment pH from said first pH range to said second pH range.

2. The system of claim 1 wherein said enzyme is sequestered by said insoluble material, and wherein a signal representative of said component concentration is capable of communicating between aqueous medium surrounding said insoluble phase and said enzyme.

3. The system of claim 2 wherein said signal comprises said component, and an increase in said component concentration causes said enzyme to change said pH from said first pH range to said second pH range.

4. The system of claim 1 wherein said component comprises a substrate for said enzyme; wherein said enzyme catalyzes formation of a product from said substrate, said product effecting said pH change.

5. The system of claim 2 wherein said insoluble material is an aqueous-permeable membrane that is permeable to said dissolved protein, but not permeable to said enzyme, and agglomerated protein being contained within said membrane.

6. The system of claim 2 wherein said insoluble material is a polymer matrix, said protein and said enzyme being interspersed therein.

7. The system of claim 6 wherein said polymer matrix is selected from ethylene vinyl acetate copolymer, nitrocellulose, silicone, hydrogels, poly-2-hydroxy ethyl methylmethacrylate, polyesters, and polyurethanes.

8. The system of claim 1 wherein said insoluble material is selected from an ethylene vinyl acetate copolymer.

9. A system providing feedback-responsive release of an insulin to an aqueous biological fluid, said system comprising,
(a) an insulin having an isoelectric point of pH 7.0 or greater;
(b) an aqueous insoluble biocompatible material positioned to sequester said insulin, said insoluble biocompatible material being characterized in that it is aqueous-fluid-penetrable, release of said insulin from said biocompatible material being directly related to insulin solubility; and
(c) an enzyme that operates in the presence of glucose to increase the solubility of said insulin.

10. The system of claim of claim 9 in which said enzyme is glucose oxidase and the insulin is modified to increase its isoelectric point.

11. The system of claim 10 further comprising polylactic acid.

12. The system of claim 1 wherein said system is adapted to be implanted, in vivo, in a mammal.

13. The system of claim 12 wherein said protein is a hormone.

14. The system of claim 13 wherein said hormone is selected from insulin, glucagon, growth hormone, lutinizing hormone, and releasing hormone.

15. The system of claim 6 wherein said protein is agglomerated and its ability to pass through said polymer matrix is restricted by said agglomeration.

16. The system of claim 15 wherein said pH change alters the ability of said protein to pass through said matrix.

17. The system of claim 1 wherein said protein is an insulin.

18. The system of claim 1 wherein said component is glucose, and said enzyme catalyzes a reaction of glucose that changes said microenvironment pH from said first range to said second range.

19. The system of claim 1 or claim 18 wherein said protein is an insulin having an isoelectric point of pH 7.0 or greater.

20. The system of claim 19 wherein said modified insulin is trilysine insulin or triglycine insulin.

21. The system of claim 19 wherein said first pH range is around the isoelectric point of said insulin and said second pH range is under 7.0.

22. The system of claim 1 wherein said component is glucose.

23. The system of claim 18 wherein said enzyme comprises glucose oxidase and catalyses production of gluconic acid from glucose.

24. The system of claim 23 wherein said first pH range is 7.5–7.1 and said second pH range is under 7.0.

25. The system of claim 23 wherein said system further comprises a means for reducing the concentration of hydrogen peroxide produced by glucose oxidase.

* * * * *